United States Patent

Groenewegen

[11] Patent Number: 5,989,581
[45] Date of Patent: Nov. 23, 1999

[54] DRUG DELIVERY SYSTEM FOR TWO OR MORE ACTIVE SUBSTANCES

[75] Inventor: Rudolf Johannes Joseph Groenewegen, Heesch, Netherlands

[73] Assignee: Akzo Nobel N.V., Arnhem, Netherlands

[21] Appl. No.: 09/056,700

[22] Filed: Apr. 8, 1998

[30] Foreign Application Priority Data

Apr. 11, 1997 [EP] European Pat. Off. .............. 97201098

[51] Int. Cl.⁶ ........................................ A61F 13/02
[52] U.S. Cl. .......................... 424/433; 424/430; 424/432
[58] Field of Search ................................ 424/430, 432, 424/433

[56] References Cited

FOREIGN PATENT DOCUMENTS 0279982  8/1988  European Pat. Off. .
WO 97/02015  1/1997  WIPO .

Primary Examiner—C. Azpuru
Attorney, Agent, or Firm—Gregory R. Muir

[57] ABSTRACT

The present invention is dealing with a drug delivery system, preferably in a ring-shaped form suitable for vaginal administration, for the simultaneous release of a progestogenic steroid compound and an estrogenic steroid compound in a fixed physiological ratio over a prolonged period of time. The drug delivery system comprises at least one compartment comprising a thermoplastic polymer core containing the mixture of the progestogenic and estrogenic compounds and a thermoplastic polymer skin, the progestogenic compound being initially dissolved in the polymer core material in a relatively low degree of supersaturation.

11 Claims, 1 Drawing Sheet

DRUG DELIVERY SYSTEM FOR TWO OR MORE ACTIVE SUBSTANCES

BACKGROUND OF THE INVENTION

The present invention relates to a drug delivery system for the simultaneous release of two or more active substances and more particularly to a ring shaped vaginal drug delivery system, which system releases the active substances in a substantially constant ratio over a prolonged period of time.

Such release system is for example known from U.S. Pat. Nos. 3,995,633 and 3,995,634, where separate, preferably spherical or cylindrical, reservoirs containing different active substances are assembled in specially constructed holders. Such a release system is also described in U.S. Pat. No. 4,237,885, where a tube or coil of polymeric material is divided into portions by means of a plurality of "spacers" provided in the tube, after which each of the separate tube portions is filled with a different active substance in a silicone fluid and the two ends of the tube are subsequently connected to one another. In this release system, however, transport (diffusion) of active material from one reservoir to the other takes place through the wall of the tube, especially upon prolonged storage, so that the pre-set fixed release ratio between the active substances in question will change over a period of time.

A two-layered vaginal ring has been described in European patent publication 0,050,867 which ring comprises a pharmacologically acceptable supporting ring covered by two layers preferably of silicone elastomers whereby the inner layer is a silicone elastomer loaded with an active substance.

A similar ring shaped vaginal delivery system had been described in U.S. Pat. No. 4,292,965. The use of silicone elastomers is nowadays considered to be less safe and is clearly no longer the material of choice.

In U.S. Pat. No. 4,596,576 a two-compartment vaginal ring has been disclosed, wherein each compartment contains a different active substance. To achieve a suitable ring with a constant release ratio between the various active substances, it was necessary, however, to join the endportions of the compartments by inert stoppers, preferably glass stoppers.

Patent Publication WO 97/02015 discloses a two-compartments device, a first compartment consisting of a core, a medicated middle layer and a non medicated outer layer, and a second compartment consisting of a medicated core and a non medicated outer layer.

Release systems which over a lengthy period release two or more active substances in a substantially constant ratio to one another are extremely useful for certain applications. For example, in the field of contraception and in the field of hormone replacement therapy, extensive use is made of the simultaneous administration of an agent having a progestogenic activity and an agent having an estrogenic activity, preferably in a substantially constant ratio.

The simultaneous introduction of these two drugs into one reservoir can however only purely accidentally lead to the desired release ratio. In fact, the release per unit time is determined by the solubility of the active substance in the outer layer of polymeric material (which forms the wall of the reservoir) and by the diffusion coefficient of the active substance in that outer layer. In this type of release system, in fact, the choice of the outer layer material of the reservoir determines the release ratio of the active substances contained in the reservoir to a large extent.

Though theoretically it is possible to choose from among a very large variety of polymeric materials, it is found in practice that only a relatively small number of polymers seem to be capable of functioning satisfactorily as a release determining outer layer of the reservoir. Not only does the medical use impose certain requirements on the polymer but in addition a large number of polymers are unsuitable in that, for example, they possess insufficient rigidity, are insufficiently inert, provide insufficient solubility of the active substance(s), etc.

Moreover, the composition of the reservoir containing the active substances is likewise important because the reservoir material is responsible for an adequate supply of the active substances to the inner side of the outer layer. The reservoir material may not shrink upon release of the active substances, must be capable of taking up a large amount of the active substances, etc.

In most cases one is therefore forced to choose a release system with a plurality of separate reservoirs as a release system which is capable of releasing two or more active substances in a particular ratio as is clearly demonstrated in the above mentioned references. Apart from a not always satisfactory release, release ratio and release term in some cases, the disclosed vaginal rings all suffer from being relatively complicated, making them more expensive to manufacture.

SUMMARY OF THE INVENTION

Surprisingly, applicant has found that a reliable release ratio over a prolonged period of time can be achieved using a one-compartment, preferably ring shaped, drug delivery system for at least two steroidal compounds (such as a progestogen and an estrogen) and more preferably for etonogestrel and ethinylestradiol by carefully selecting and treating the reservoir and outer layer materials.

The preferably ring-shaped drug delivery system according to the present invention (hereinafter called vaginal ring) comprises at least one compartment comprising a thermoplastic polymer core containing at least the progestogenic steroidal compound and the estrogenic steroidal compound in a ratio by weight that allows a direct release from the said polymer of both the progestogenic compound and the estrogenic compound in physiologically required amounts, said progestogenic compound being initially dissolved in the core polymer in a relatively low degree of supersaturation, preferably being 1 to about 6 times of the amount by weight necessary for obtaining the saturation concentration of said progestogenic steroid in said core polymer at 25° C., said estrogenic compound being initially dissolved in the core polymer in a concentration being lower than that of the said progestogenic compound, and a thermoplastic skin (outer layer) being permeable for the said progestogenic and estrogenic compounds.

More particularly a vaginal ring according to the invention preferably to be used for contraception comprises at least one compartment comprising a thermoplastic polymer core of ethylene-vinylacetate copolymer (poly-EVA) containing at least etonogestrel (3-keto desogestrel) as the progestogenic compound and ethinylestradiol as the estrogenic compound in a ratio by weight of about 10 parts of etonogestrel and about 1.5–5 parts of ethinylestradiol, whereby the compound etonogestrel is dissolved in the poly-EVA core in an amount by weight of at least 1 but not more than about 6 times and more preferably between 2 and 5 times the amount necessary for obtaining its saturation concentration at 25° C., and a thermoplastic skin of poly-EVA being permeable for both etonogestrel and ethinylestradiol.

As may be derived already from the above description the present invention is based on the surprising finding that a steroid can be retained in a supersaturated state during prolonged storage (such as 6 months or longer) at temperatures between 4° C. and 25° C., provided that the steroid concentration does not exceed the solubility at 25° C. excessively. Of course, the allowable excess is determined by the lowest storage temperature, the steroid compound, and the thermoplastic polymer including any additional compounds present (cosolvent effect). If however the said excess exceeds the allowable limits the steroid crystallises out on the exterior surface of the vaginal ring.

This finding allows for a vaginal ring which can be easily manufactured, and which provides for the reliable and predictable release of the steroid compounds. In contrast to known vaginal rings comprising a steroid-containing fluid core, the solid thermoplastic core of present vaginal ring does not bring with it the risk of leakage of steroid-comprising fluid, for example due to a failing seal. In addition, the present vaginal rings can be manufactured with extrusion techniques easily and cheaply. The manufacture of a complicated device, that is, comprising compartments differing both in the number of layers and in steroid composition, is circumvented.

The thermoplastic polymer that can be used in practising the invention, may in principle be any thermoplastic polymer or elastomer material suitable for pharmaceutical use, such as low density polyethylene, ethylene-vinylacetate copolymers and styrene-butadiene-styrene copolymers. The ethylene-vinylacetate copolymer (poly-EVA) is highly preferred due to its excellent mechanical and physical properties (e.g. solubility of the steroids in the material). The poly-EVA material may preferably be used for both the core as well as the skin and can be any commercially available ethylene-vinylacetate copolymer, such as the products available under the trade names: Elvax, Evatane, Lupolen, Movriton, Ultrathene and Vestypar.

The vaginal ring according to the invention can be manufactured in any size as required. In practice, however, the ring has an outer diameter of between 50 and 60 mm and more preferably between 52 and 56 mm; the cross sectional diameter is preferably between about 2.5 and 5 mm.

The surface of the core body is preferably more than 800 mm$^2$, more preferably at least 1000 mm$^2$ and will typically be in the order of 1700–2000 mm$^2$, though significantly larger surfaces are possible, provided that the design (physical dimensions) of the vaginal ring prevents inconvenience for the subject. Although not preferred it may sometimes be required to add a second compartment which is a placebo compartment or a compartment loaded with one or more other drugs. Such an extra compartment may be necessary for example in practising hormonal replacement therapy, where the ratio between progestogen and estrogen is different from the ratio suitable for contraception. A vaginal ring comprising only one compartment, however, is the preferred embodiment of this invention; it is easy to manufacture and shows an adjustable and excellent release pattern.

The vaginal ring according to the invention is primarily designed for contraceptive use, but—as said above—may also be used under certain conditions in HRT (hormonal replacement therapy). The progestogenic steroidal compound can be any suitable progestogen, such as desogestrel, etonogestrel, levonorgestrel, norgestimate, gestodene or any other steroidal compound with progestogenic activity. The estrogenic steroidal compound can be any suitable estrogen, such as estradiol, estriol, mestranol and ethinylestradiol. The preferred progestogen is etonogestrel. The preferred estrogen for contraceptive use is ethinylestradiol whereas estradiol is the preferred estrogen for HRT.

For contraception in humans, the vaginal ring according to the present invention is preferably characterised in that the poly-EVA core body comprises etonogestrel and ethinyl estradiol in about a 1 to 0.2–0.4, more preferably in a 1 to 0.2–0.3, ratio by weight, whereby etonogestrel is dissolved in the poly-EVA material up to a relatively low degree of supersaturation, preferably 1 to 6 times its saturation concentration at 25° C., so as to allow over a period of 21 days an average release rate of 95 to 145 $\mu$g, preferably 120 $\mu$g, etonogestrel and 10–20 $\mu$g, preferably 15 $\mu$g, ethinyl estradiol per 24 hours in situ.

In an advantageous embodiment of such a vaginal ring, the skin is an ethylene-vinylacetate copolymer skin having a thickness ranging from 40 to 300 $\mu$m and a vinyl acetate content ranging from 5 to 15%, and more in particularly the skin of the compartment has a thickness of 110 $\mu$m and is comprised of ethylene-vinylacetate copolymer with a 9% to 10% vinyl acetate content.

Such a skin has excellent solubility and steroid diffusion properties, allowing the combined release of etonogestrel and ethinyl estradiol in the proper ratio at moderate concentrations of the steroids in the vaginal ring during a prolonged period of time.

In addition, the core body is advantageously comprised of a ethylene-vinyl acetate copolymer with a 25 to 35%, preferably 26 to 30% vinyl acetate content. The percentage vinyl acetate can be established using potentiometric titration as described in various textbooks on this subject matter.

As said earlier it is an essential element of the present invention to have the progestogenic steroid dissolved in the core material in a relatively low degree of supersaturation. This "relatively low degree of supersaturation" may generally be defined as the amount of progestogenic steroid that is one to about six times the amount necessary to obtain the saturation concentration of the steroid in the polymer at 25° C. and more preferably from 2 to 5 times.

The saturation concentration of the steroid can be determined by various methods known per se in the art. For instance the thermoplastic polymer is introduced in a saturated solution of the steroid (provided with additional steroid crystals) at 25° C. and kept in that saturated solution until the concentration of the steroid in the polymer remains constant. Another suitable method for the determination of the saturation concentration is the so called time-lag method.

In a more preferred embodiment of the invention wherein the progestogenic steroidal compound is etonogestrel, the estrogenic compound is ethinyl estradiol and the core material is poly-EVA, a "low degree of supersaturation" is obtained by using a quantity of etonogestrel in said poly-EVA core material of from about 0.3 to about 1% by weight, the quantity of ethinyl estradiol then being from about 0.05 to about 0.3% by weight. With such initial low degree of supersaturation the etonogestrel containing vaginal ring is surprisingly stable.

The poly-EVA core may advantageously comprise 0.5 to 1%, preferably 0.55 to 0.8% by weight of etonogestrel and 0.10 to 0.23%, preferably 0.12–0.18% by weight of ethinyl estradiol.

At these preferred steroid concentrations in the core material, the skin specified above allows for the combined release of etonogestrel and ethinyl estradiol at the proper physiological rate for a prolonged period of time, whereby the drug delivery device—the vaginal ring—shows excellent stability (no crystallisation on the exterior surface of the ring) upon storage during a considerable period of time.

The vaginal ring according to the invention can be manufactured in any suitable manner. A preferred method of manufacture comprises co-extrusion of the drug-loaded core and the non-medicated outer layer. The fibres thus obtained are cut into pieces of the required length and each piece is assembled to a ring shaped device in any suitable manner. The rings are then packed for example in a suitable sachet, optionally after being sterilised or disinfected.

BRIEF DESCRIPTION OF THE DRAWINGS

The invention is further illustrated by the following examples, describing the manufacture of a vaginal ring according to the invention.

DESCRIPTION OF THE PREFERRED EMBODIMENTS

Figure 1:
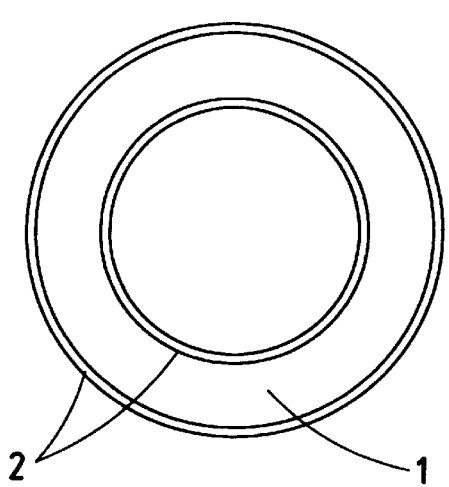
FIG. 1 shows a planar cross-sectional view of a first embodiment of a vaginal ring according to the present invention.
Figure 2:
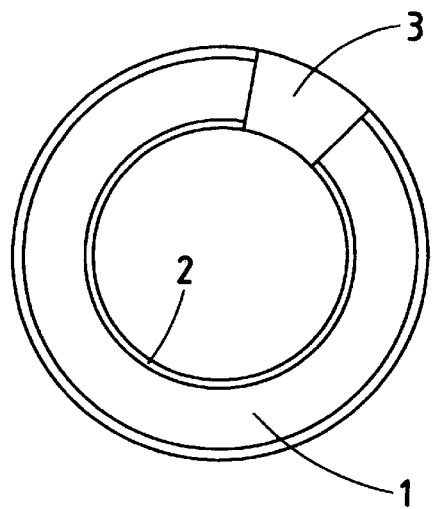
FIG. 2 shows a planar cross-sectional view of a second embodiment of a vaginal ring according to the present invention.
Figure 3:
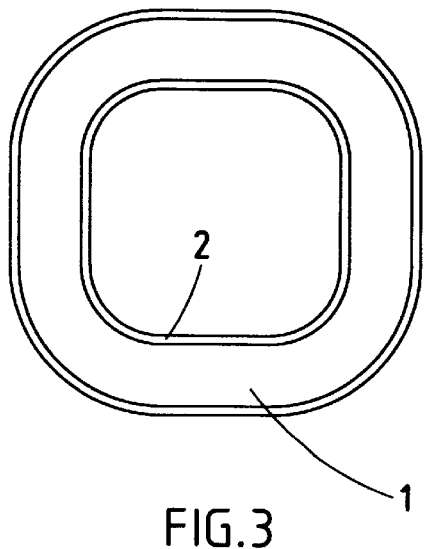
FIG. 3 shows a planar cross-sectional view of a third, non circular embodiment of a vaginal ring according to the present invention.
Figure 4:
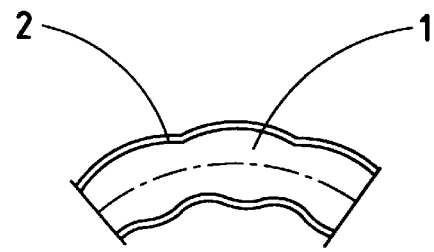
FIG. 4 shows a partial planar cross-sectional view of a fourth embodiment of a vaginal ring according to the present invention provided with ondulations.

FIG. 1 shows a vaginal ring with a core body (1) and a skin (2) which covers the core body (1) and controls the release rate. As shown in FIG. 3, the ring is not necessarily a perfectly circular object, whereas the section of a vaginal ring according to the invention shown in FIG. 4 demonstrates that the ring may involve a surface-enlarging design. FIG. 2 illustrates that another body (3) may be incorporated as part of the ring.

EXAMPLE 1

57 Parts of etonogestrel, 12 parts of ethinyl estradiol (EE), 5 parts of magnesium stearate and 9926 parts of Evatane® 28-25 are mixed. This mixture is coextruded with Evatane® 1020 VN3 to form a co-axial fibre with an outer diameter of 4,0 mm and a skin thickness of 80 µm. The fibre is cut into pieces of 157 mm. Subsequently, the ends of the fibre pieces are joined by using an adhesive (FIG. 1).

The ring obtained is stored at 25° C. and at ambient relative humidity (RH) for 6 months after which the amount of steroids on the outer surface is determined by rinsing with methanol and subsequent HPLC analysis. The amount of steroid on the ring surface is less than 10 µg etonogestrel and less than 2 µg ethinyl estradiol, which is considered very small and comparable to the zero time situation. This example shows that even with etonogestrel at a relatively low degree of supersaturation, a stable dosage form can be obtained.

EXAMPLE 2

75 parts of etonogestrel, 16 parts of ethinyl estradiol, 5 parts of magnesium stearate and 9904 parts of Evatane® 28-25 are mixed. This mixture is coextruded with Evatane® 1020 VN3 to form a co-axial fibre with an outer diameter of 3,5 mm and a skin thickness of 90 µm. The fibre is cut into pieces of 147 mm. Subsequently, the two ends of each fibre piece are joined by using an adhesive.

The ring obtained is stored at 25° C./ambient RH for 6 months after which the amount of steroids on the outer surface is determined by rinsing with methanol and subsequent HPLC analysis. The amount of steroid on the ring surface is less than 10 µg etonogestrel and less than 2 µg ethinyl estradiol, which is considered very small and comparable to the zero time situation.

EXAMPLE 3

According to the procedure of Example 1, ring-shaped devices were prepared with the characteristics listed in Table 1. It should be noted that the saturation concentration of etonogestrel was determined at 25° C., using a dissolution test, and is 0.35%. In the dissolution test, the solubility of the active substances etonogestrel and ethinyl estradiol in the core polymer (Evatane® 28-25) is determined by saturating flat films (thickness 200 µm) with saturated aqueous solutions of said active substances, using a (shaking) incubator. After 4 and 6 weeks, the films were analysed for steroid content. The two periods of time were chosen in order to ensure that the maximum saturation is reached (which can be concluded from the fact that no significant difference between 4 and 6 weeks is found). The values at 25° C. are about 0.35% for etonogestrel and about 1.30 for ethinyl estradiol.

TABLE 1

| Characteristics of vaginal rings | | | | | |
|---|---|---|---|---|---|
| Fibre diameter | Skin thickness | Core load (% by weight) | | | Fibre length |
| (m) | (µm) | Etonogestrel | EE | Mg stearate | (mm) |
| 4,0 | 70 | 0,57 | 0,12 | 0,05 | 147 |
| 4,0 | 90 | 0,57 | 0,12 | 0,05 | 157 |
| 3,5 | 80 | 0,75 | 0,16 | 0,05 | 147 |
| 3,5 | 100 | 0,75 | 0,16 | 0,05 | 157 |
| 4,0 | 100 | 0,69 | 0,16 | 0,05 | 157 |
| 4,0 | 110 | 0,69 | 0,16 | 0,05 | 157 |
| 4,0 | 120 | 0,69 | 0,16 | 0,05 | 157 |
| 4,0 | 100 | 0,73 | 0,17 | 0,05 | 147 |
| 4,0 | 110 | 0,73 | 0,17 | 0,05 | 147 |
| 4,0 | 120 | 0,73 | 0,17 | 0,05 | 147 |

EXAMPLE 4

57 Parts of etonogestrel, 12 parts of ethinyl estradiol, 5 parts of magnesium stearate and 9926 parts of Evatane® 28-25 are mixed. This mixture is coextruded with Evatane® 1020 VN3 to form a co-axial fibre with an outer diameter of 4.0 mm and a skin thickness of 90 µm. The fibre is cut into pieces of 147 mm. The fibre piece is placed in a mould at a temperature of 40° C., the ends of a fibre piece are joined by injecting molten high density polyethylene (HDPE) in between the fibre ends and subsequently cooled. FIG. 2 shows the HDPE body (3) joining the ends of the skin (2)-covered core body (1).

EXAMPLE 5

69 Parts of etonogestrel, 16 parts of ethinyl estradiol, 5 parts of magnesium stearate and 9910 parts of Evatane® 28-25 are mixed. This mixture is coextruded with Evatane® 1020 VN3 to form a co-axial fibre with an outer diameter of 4.0 mm and a skin thickness of 110 µm. The fibre is cut into pieces of 157 mm. Subsequently, the ends of the fibre pieces are joined by welding.

REFERENCE EXAMPLE

500 Parts of etonogestrel, 500 parts of ethinyl estradiol and 9000 parts of Evatane® 28-25 are mixed. This mixture is coextruded with Evatane® 1080 VN5 to form co-axial fibres with an outer diameter of 2.75 mm and different skin thicknesses. The fibres are stored at room temperature after which the amount of steroids on the outer surface is determined by rinsing with methanol and subsequent HPLC analysis. The amounts of steroids on the fibre surface are given in Table 2. This example clearly shows that at a high degree of supersaturation, no stable dosage form can be obtained.

TABLE 2

Amount of steroids on surface of fibres to be used in the manufacturing of vaginal rings

| Skin thickness ($\mu$m) | Storage time at room temp./amb. RH (months) | Etonogestrel ($\mu$g/157 mm) | Ethinyl estradiol ($\mu$g/157 mm) |
| --- | --- | --- | --- |
| 128 | 6 | 450 | 80 |
| 128 | 8 | 1530 | 175 |
| 210 | 29 | 1800 | 215 |
| 221 | 39 | 1490 | 370 |
| 133 | 75 | 1830 | 195 |

I claim:

1. A drug delivery system comprising at least one compartment which comprises a thermoplastic polymer core and a thermoplastic polymer skin covering the core, said core comprising a mixture of a steroidal progestogenic compound and a steroidal estrogenic compound in a ratio by weight that allows a direct release of both said progestogenic compound and said estrogenic compound in physiologically required amounts, said progestogenic compound being initially dissolved in said polymer core material in a degree of supersaturation of 1 to about 6 times of the amount by weight necessary for obtaining saturation concentration of said progestogenic compound in said polymer core material at 25° C., said estrogenic compound being dissolved in said polymer core material in a concentration lower than that of said progestogenic compound, and said thermoplastic skin being permeable for said progestogenic and estrogenic compounds.

2. A drug delivery system according to claim 1, wherein the delivery system has a substantially ring-shaped form and is intended for vaginal administration of the mixture of the progestogenic and estrogenic compounds.

3. A drug delivery system according to claim 1, wherein at least the skin material comprises ethylene-vinylacetate copolymer as the thermoplastic polymer.

4. A drug delivery system according to claim 1, wherein the amount of progestogenic compound dissolved in the thermoplastic core material is 2 to 5 times the amount necessary for obtaining saturation concentration.

5. A drug delivery system in a substantially ring-shaped form and suitable for vaginal administration comprising at least one compartment which comprises a thermoplastic polymer core and a thermoplastic polymer skin covering said core, said core comprising a mixture of a progestogenic steroidal compound and an estrogenic steroidal compound in a ratio by weight of 10 parts of the progestogenic compound to 1.5–5 parts of the estrogenic compound, said progestogenic compound being initially dissolved in said polymer core in a degree of supersaturation of 1 to about 6 times of the amount by weight necessary for obtaining saturation concentration of said progestogenic compound in said polymer core material at 25° C., and said polymer skin being permeable for both the progestogenic and the estrogenic compounds.

6. A drug delivery system according to claim 5, wherein the thermoplastic polymer used for the core material is an ethylene-vinylacetate copolymer, the thermoplastic polymer used for the skin material is an ethylene-vinylacetate copolymer, the thermoplastic polymer used for the skin material is an ethylene-vinylacetate copolymer, said core comprising a mixture of a progestogenic compound etonogestrel and an estrogenic compound ethinylestradiol in a ratio of 10 parts to 2–4 parts, said core comprising from 0.3 up to about 1% by weight of etonogestrel and from about 0.05 to about 0.3% by weight of ethinyl estradiol.

7. A drug delivery system according to claim 6, wherein the ratio of etonogestrel to ethinylestradiol is 10 parts to 2–3 parts, the weight percentage of etonogestrel being 0.5% and 1.0%.

8. A drug delivery system according to claim 6, characterised in that the skin is an ethylene-vinylacetate copolymer skin having a thickness ranging from 40 to 300 $\mu$m and a vinylacetate content ranging from 5 to 15%.

9. A drug delivery system according to claim 8, characterised in that the skin thickness is 80 to 150 $\mu$m and the vinyl acetate content is 9–10%.

10. A drug delivery system according to claim 5, wherein the core material is comprised of an ethylene-vinylacetate copolymer with a 25 to 35% vinyl acetate content.

11. A drug delivery system according to claim 5, wherein the core material comprises 0.55 to 0.8% by weight of etonogestrel and 0.12 to 0.18% by weight of ethinyl estradiol.

* * * * *